(12) United States Patent
Flores et al.

(10) Patent No.: US 10,462,830 B2
(45) Date of Patent: Oct. 29, 2019

(54) PROXIMITY ENABLED COMMUNICATION NETWORK SYSTEM FOR PERIPHERAL DEVICE

(71) Applicants: Robert G Flores, Richmond Hill, NY (US); Navaneet Pandurangan, Edison, NJ (US)

(72) Inventors: Robert G Flores, Richmond Hill, NY (US); Navaneet Pandurangan, Edison, NJ (US)

(*) Notice: Subject to any disclaimer, the term of this patent is extended or adjusted under 35 U.S.C. 154(b) by 298 days.

(21) Appl. No.: 15/494,921

(22) Filed: Apr. 24, 2017

(65) Prior Publication Data

US 2018/0310345 A1    Oct. 25, 2018

(51) Int. Cl.

| | |
|---|---|
| *H04W 76/14* | (2018.01) |
| *H04W 8/00* | (2009.01) |
| *H04L 29/08* | (2006.01) |
| *H04W 4/80* | (2018.01) |
| *H04W 4/02* | (2018.01) |
| *H04W 4/21* | (2018.01) |
| *A61B 5/16* | (2006.01) |
| *A61B 5/00* | (2006.01) |

(52) U.S. Cl.
CPC .............. *H04W 76/14* (2018.02); *H04L 67/06* (2013.01); *H04L 67/18* (2013.01); *H04W 4/023* (2013.01); *H04W 4/21* (2018.02); *H04W 4/80* (2018.02); *H04W 8/005* (2013.01); *A61B 5/0022* (2013.01); *A61B 5/165* (2013.01); *H04W 4/026* (2013.01); *H04W 4/027* (2013.01)

(58) Field of Classification Search
CPC ....... H04W 76/14; H04W 4/80; H04W 8/005; H04W 4/026; H04W 4/027; G16H 10/00; H04L 67/06; H04L 67/18; A61B 5/0022; A61B 5/165
See application file for complete search history.

(56) References Cited

U.S. PATENT DOCUMENTS

| | | | | |
|---|---|---|---|---|
| 9,280,849 | B2* | 3/2016 | Adhikari | G06Q 30/0623 |
| 10,146,414 | B2* | 12/2018 | Heater | G06F 3/04845 |
| 10,217,340 | B2* | 2/2019 | Lerner | G06K 7/10366 |
| 2015/0281323 | A1* | 10/2015 | Gold | H04M 1/7253 |
| | | | | 715/740 |
| 2015/0378547 | A1* | 12/2015 | Pesonen | G09B 5/00 |
| | | | | 345/156 |

* cited by examiner

*Primary Examiner* — Kibrom T Hailu
(74) *Attorney, Agent, or Firm* — Williams Intellectual Property; Benjamin F. Williams

(57) ABSTRACT

A proximity enabled communication network system for peripheral device is provided enabling line of sight communications between users. A radiant pointing device is contemplated to enable orientation of a vector drawn from a known unique user location established over network, whereby incidence of a radiant emission from the radiant pointing device against an object or another user enables determination of a unique object location or the location of the other user. Object data may be storable and accessible over network pertaining to each unique object location and profile data may be storable and uploadable over network pertaining to each user operating in the network. The object data may be downloadable to user WCDs when effecting incidence of the radiant emission against an associated object whereby information is sharable encoded to specific object locations. Further, information pertinent to each user may likewise be sharable between users operating in the network.

14 Claims, 9 Drawing Sheets

PROXIMITY ENABLED COMMUNICATION NETWORK SYSTEM FOR PERIPHERAL DEVICE

COPYRIGHT NOTICE

Some portions of the disclosure of this patent document may contain material subject to copyright protection. The copyright owner has no objection to the facsimile reproduction by anyone of the patent document or ensuing disclosure as it appears on record at the Patent and Trademark Office, but otherwise reserves all copyright rights whatsoever.

BACKGROUND OF THE INVENTION

Various types of proximity enabled communication network systems are known in the prior art. Most enable determination of user location relative a known geospatial landscape. What is needed is a proximity enabled communication network system for peripheral device that enables establishment of line of sight communication between users whereby information pertinent to users and particular objects determinable in network is sharable between users operating a radiant pointing device to tag each other, and to tag objects of interest, whereby unique user locations and unique object locations are determinable relative each user operating in network.

FIELD OF THE INVENTION

The present invention relates to a proximity enabled communication network system for peripheral device, and more particularly, to a proximity enabled communication network system for peripheral device that includes determination of a unique user location wherefrom a vector is to measurable when a radiant emission emitted from a radiant pointing device is sensed incident a particular object whereby unique object locations are determinable relative a known user location. Determination of a specific location relative a known user location by action of the radiant pointing device is termed "tagging".

Object data is uploadable, storable, and accessible over the network, whereby a user may effect display or execution of data files downloaded over network to a user WCD by act of tagging an object or another user. Users may thus share location and object specific information as object data accessible to all users tagging an associated object having a unique object location.

Further, users are enabled to tag each other when in line of sight, whereby profile data is sharable between users. Users may push tag prompts to other user WCDs when tagging said other users, which tag prompts may display as a message or an alarm signal. P2P communication between users is establishable when mutually assented by each user participating in the network and desirous to interact.

In one embodiment, at least one biometric sensor is contemplated in sensing contact with each user whereby an emotional state and emotional response is communicable over network whereby users tagging each other and participating in the network may determine and share emotional states and responses, as desired.

SUMMARY OF THE INVENTION

The term "WCD", as used herein throughout, stands for "Wireless Communications Device" and is taken to include all such devices as are capable of connecting wirelessly to exchange data over a network. Thus handheld computing devices, tablets, peripheral devices, laptops, smart phones, and other wirelessly operable computing devices are intended under scope of the term. Additionally, devices sensible over network, such as Radio Frequency Identification tags ("RFIDs"), where capable of relaying specific location data and other identifying data over network, are also included.

The term "P2P" is taken to include all peer-to-peer communication protocols whereby one user may communicate directly to another user, whether by Near Field Communication ("NFC") protocol or via cellular or other network. The term "NFC" is taken to include all communication protocols contingent upon proximity between WCDs such as, for example, Bluetooth®.

A proximity enabled communication network system for peripheral device operable between users in line-of-sight and determined by locational proximity when interconnected via network is herein provided, whereby users operating unique WCDs may establish communication with each other and exchange pertinent information over network and via P2P when determined to be proximal each other and, alternately, when tagged by a user operating a radiant pointing device. The radiant pointing device is devised to be sensible of a vector relative a user, and thereby usable to determine a unique location of an object incident a radiant emission wieldable by the user, said object thereby "tagged" by the user operating the radiant pointing device. Using the radiant pointing device, a user may therefore tag an object to determine the object's unique location relative the said user, whereby object data pertinent to the tagged object, where extant over network, is downloadable to the user WCD and displayable onscreen. Information is thus sharable regarding inanimate objects having a unique object location discoverable over network relative a user's unique location. User profile data is likewise downloadable for display onscreen when a user tags another user operating within the network.

The present proximity enabled communication network system for peripheral device, therefore, includes at least a first WCD operating in network. The at least first WCD is disposed in networked communication with a central server, whereby repeating signals transmittable from the at least first WCD are determinative of a unique user location. A unique user location is therefore continuously discoverable, or monitorable at discrete intervals as may be required to maintain determination of an instantaneous unique user location.

At least one radiant pointing device is disposed in communication with the at least first WCD. The at least one radiant pointing device may be disposed in wireless communication with the WCD, such as by NFC, or the at least one radiant pointing device may be connectable to the WCD to enable data transfer therebetween. In some embodiments contemplated by the present disclosure, the at least one radiant pointing device may be connectable to a case or other covering usable in connection with the WCD wherein connection of the radiant pointing device to the case effects connection to WCD and enables data transfer therebetween.

The at least one radiant pointing device includes a directionally sensitive member whereby direction of a radiant emission controllable by a user is sensible to the associated WCD and therefore determinable over network. The directionally sensitive member may include a gyroscope, an accelerometer, or a magnetic member devised to determine a bearing. Direction of the radiant pointing device is further determinable relative a bearing object. The bearing object may be magnetic north for example, or, when present, it may be the unique object location of a previously tagged object extant in geospatial relationship sensible relative the at least first WCD.

A user operating the radiant pointing device, therefore, may direct a radiant emission incident a particular object within a line of sight, for example. A vector to the sighted object, therefore, relative the known unique user location enables determination of a unique object location. The unique object location is storable over network as an individual data point. A user may, therefore, tag an object and enter it as extant upon the network and identifiable by the unique object location.

The user may upload object data pertinent to the object to the network for read and read/write access of other users operating in the network when tagging the particular object. If the user is an originating user, that is a user originating the object to the network, then the user may lock the object data whereby other user's are entitled read only access, and are not able to edit or amend the uploaded object data pertinent to the specific unique object location. Thus a user may, for example, tag a sign for a business and then upload information pertinent to that business whereby users operating in the network are enabled acquisition of said information by subsequently tagging the object. For example, a restaurant owner may tag a menu board displayed outside said restaurant owner's storefront and upload the day's specials or other object data pertinent to the object. Users thence tagging the menu may review the object data and gain information relevant to the object at hand. Additionally, objects may be designated by an object WCD disposed associated with said object whereby the unique object location may be determinable from an object WCD communicating in network. Object data associated with the unique object, therefore, may be associable to the object WCD as well as the unique object location, where preferred.

User to user tagging is contemplated as part of this invention. A first user may likewise tag a second user operating in network to prompt display of at least a portion of a profile data corresponding to the said second user. Incidence of the radiant emission from the first user radiant pointing device enables determination of a relative location relative the first user. When said relative location matches to a known second user location, then the second user is "tagged". A tag prompt may be issued by the second user's WCD (in this instance, a second WCD) to alert the second user they have been tagged. The first user may likewise effect a push notification to the second user upon tagging the second user as part of the tag prompt, said push notification devised to relay a message or a status or at least a portion of the first user profile data, whereby the second user is made aware of being tagged, and by whom. The tag prompt may signal an alarm or read as an onscreen prompt only. The second user may likewise respond to the first user by interaction at the second user WCD, as desired, to respond to the tag via P2P communication and alternately over network. Alternately, the second user may default responses to tags initiated against them, or opt not to participate in the network until enabling participation, as desired.

In some embodiments, at least one biometric sensor is contemplated disposed in sensing contact with each user whereby an emotional response of said each user is sensible and communicable across network between users tagging each other. A first user may, therefore, receive an emotional response communicated to the first WCD, for example, after tagging a second user. Thus the first user may be apprised of the second user's emotional response to contact initiated by said first user. The emotional response may be sensed by biometrics such as, for example, pulse, body temperature, rate of breathing, among other biometrics usable to gauge an emotional state of a user.

Thus has been broadly outlined the more important features of the present proximity enabled communication network system for peripheral device so that the detailed description thereof that follows may be better understood and in order that the present contribution to the art may be better appreciated.

Objects of the present proximity enabled communication network system for peripheral device, along with various novel features that characterize the invention are particularly pointed out in the claims forming a part of this disclosure. For better understanding of the proximity enabled communication network system for peripheral device, its operating advantages and specific objects attained by its uses, refer to the accompanying drawings and description.

BRIEF DESCRIPTION OF THE DRAWINGS

Figures

DETAILED DESCRIPTION OF THE DRAWINGS

With reference now to the drawings, and in particular FIGS. 1 through 9 thereof, example of the instant proximity enabled communication network system for peripheral device employing the principles and concepts of the present proximity enabled communication network system for peripheral device and generally designated by the reference number 10 will be described.

Referring to FIGS. 1 through 9 a preferred embodiment of the present proximity enabled communication network system for peripheral device 10 is illustrated.

The present proximity enabled communication network system for peripheral device 10 has been devised to enable establishment of line of sight communication between users and other users, as well as between users and specifically tagged objects.

Figure 1:
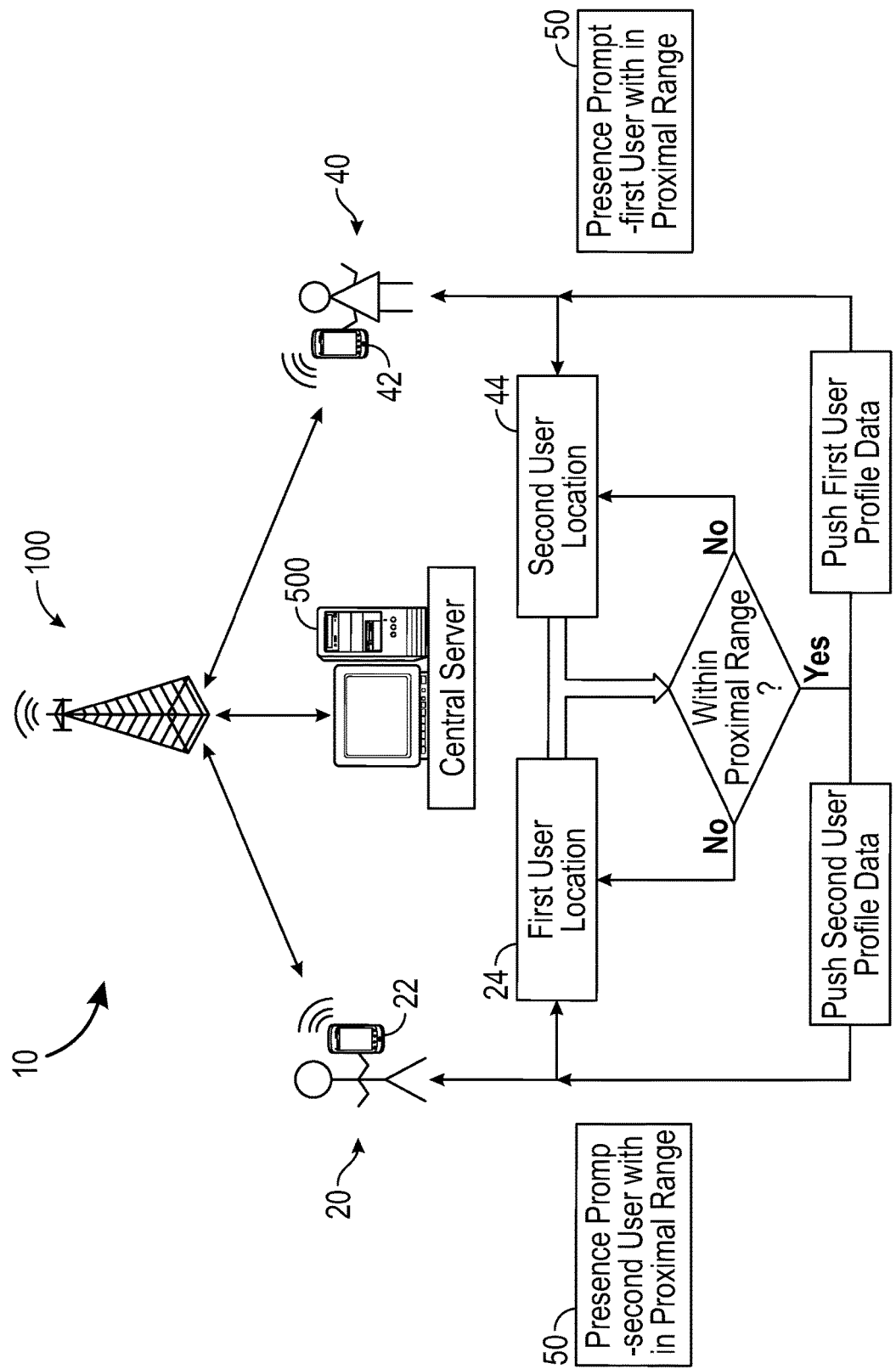
FIG. 1 is a diagrammatic view of an example embodiment of the present system.
Figure 2:
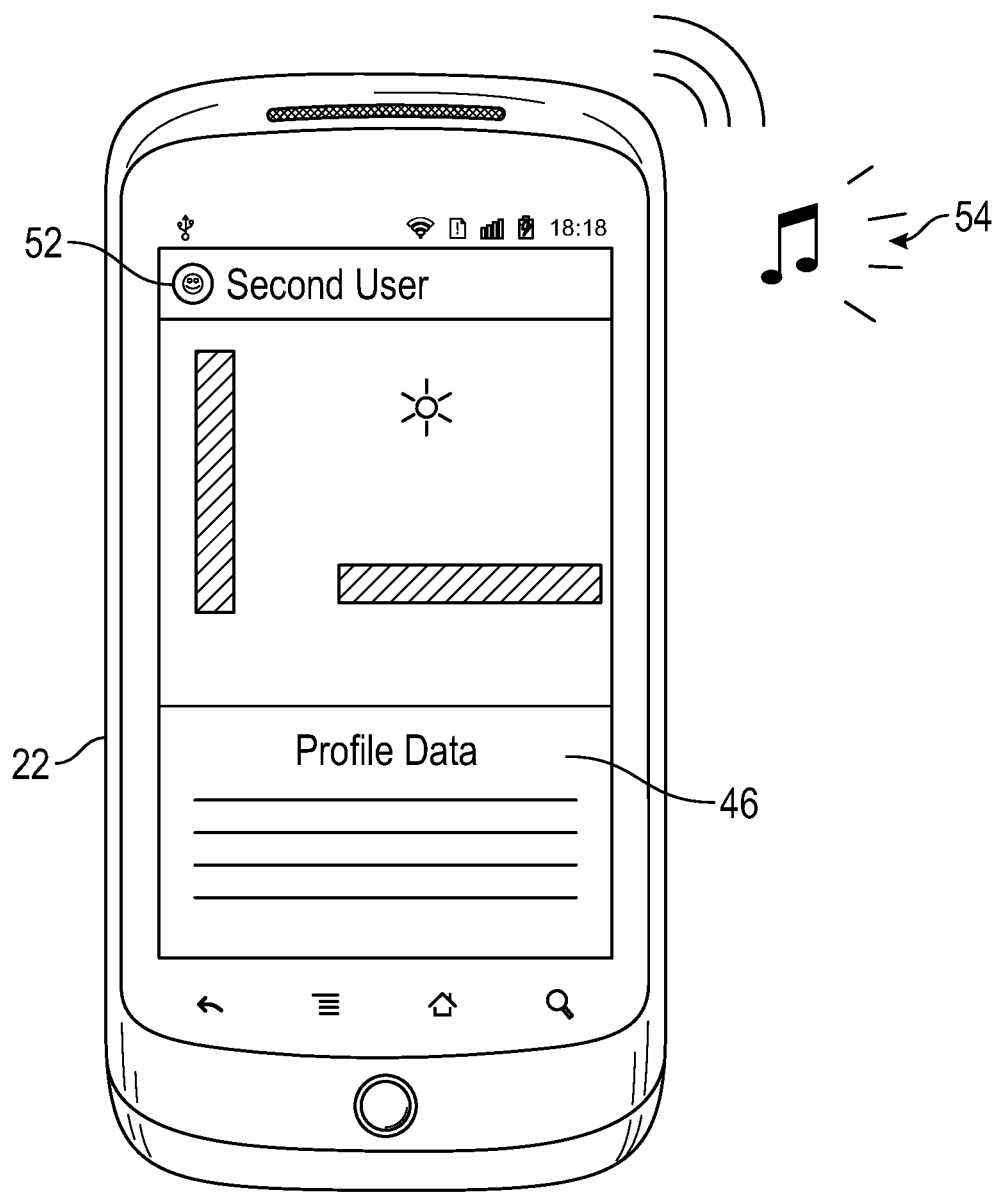
FIG. 2 is a screenshot of an example embodiment of a presence prompt displayable onscreen of a first WCD.
Figure 3:
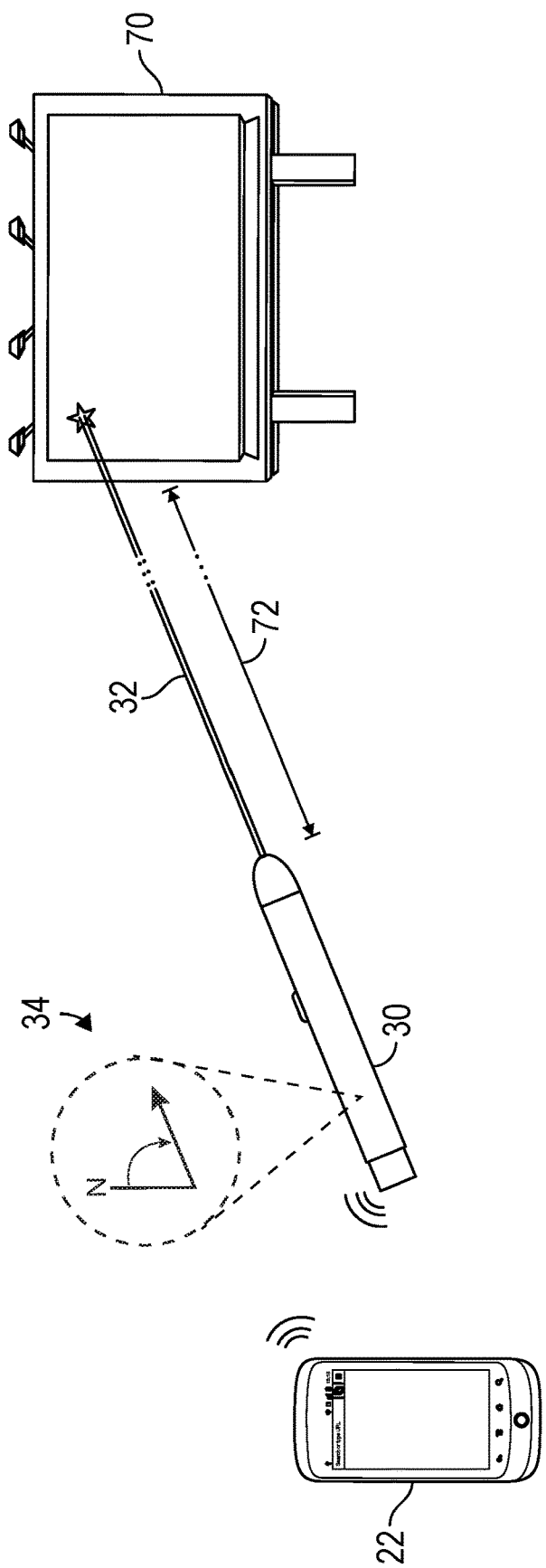
FIG. 3 is a detail diagrammatic view of an example embodiment of a radiant pointing device establishing a vector to a tagged object.
Figure 4:
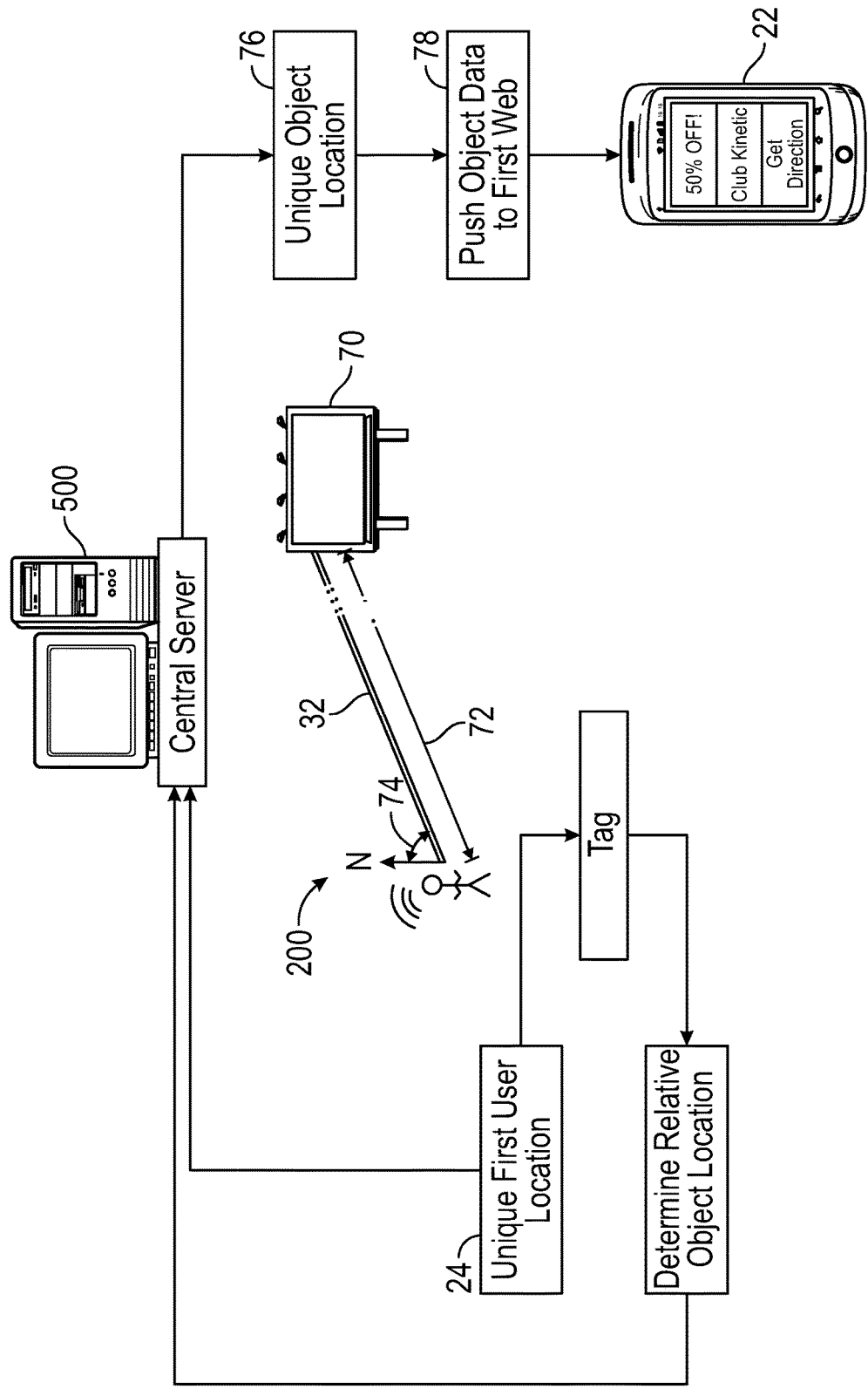
FIG. 4 is a diagrammatic view of an example embodiment of a first user tagging an object to download object data pertinent to the tagged object.

As shown in FIG. 1, the present proximity enabled communication network system for peripheral device 10 includes at least a first user 20 operating at least a first WCD 22 over a network 100. The at least first WCD 22 communicates a unique first user location 24 over the network 100 to a central server 500. A second user 40, operating a second WCD 42 over the network 100, has a unique second user location 44 also communicable over network 100. When the unique second user 44 location is determined to be within a proximal range of the unique first user location 24, a presence prompt 50 is pushed to each of the first and second WCD 22, 42 whereby each of the first user 20 and second user 40 are alerted to each other operating on the network 100 within the proximal range. As shown in FIG. 2, the presence prompt 50 may include an onscreen alert 52 or an alarm signal 54 issued from the particular WCD (the first WCD 22 in this example) receiving the presence prompt 50. At least a portion of the second user profile data 46, storable over network 100 upon the central server 500, and associated with the second user 40, is displayable onscreen upon the first WCD 22 when the second user 40 is discovered operating within the proximal range. In like manner at least a portion of a first user profile data (not shown) is displayable upon the second WCD 42. Each of the first and second user 20, 40 may thence select the displayed onscreen alert 52 to initiate contact with the selected user, as desired. P2P communication may thence be established. In the example embodiment depicted in FIG. 2 the unique second user location 44 is displayable onscreen of the first WCD 22. Additional users (not shown) may likewise be shown onscreen when discovered operating within the proximal range of the first user 20.

A radiant pointing device 30 is included in the possession of each user. In the example embodiment illustrated in FIGS. 3 and 4, the first user tags an object 70 by effecting incidence of a radiant emission 32 controllable from the radiant pointing device 30 upon the object 70, a billboard in the example shown in FIGS. 3 and 4. Reflection of the radiant emission 32 back to the radiant pointing device 30 enables determination of a distance 72 to the object 70. The radiant pointing device 30 also includes a directionally sensitive member 34 whereby a vector 74 is determinable relative the unique first user location 24. The vector 74 may be determined as an angular bearing relative a bearing object 200, for example magnetic north. A unique object location 76 is thus determinable by incidence of the radiant emission 32 against an object 70 drawn relative the unique first user location 24.

The unique object location 76 is communicable over network 100 by transmission between the central server 500 and the first WCD 22. Data stored associated with the unique object location 76 is thence transmittable to the first WCD 22 for onscreen display of object data 78 and interaction with the first user 20. In the example embodiment depicted in FIG. 4 the object data 78 is a special ticket discount for a nightclub. Directions to the club from the unique first user location 24 are also downloadable.

Figure 5:
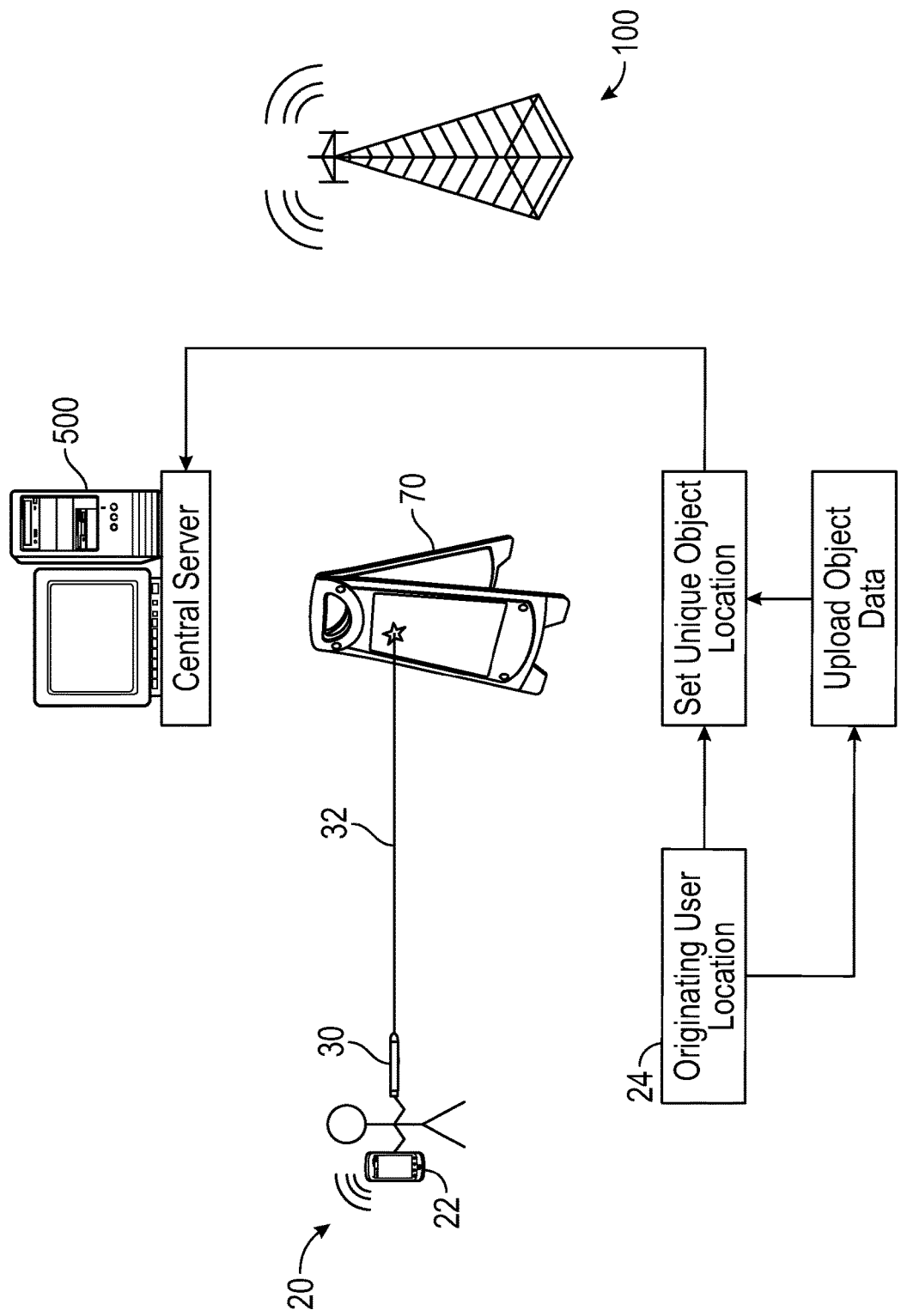
FIG. 5 is a diagrammatic view of an originating user tagging an object to set a unique object location into the system and upload pertinent metadata downloadable as object data once the object is subsequently tagged by another user.

As shown in FIG. 5, an originating user 20 may similarly tag an object 70 to store an associated unique object location 76 to memory accessible over network 100. The originating user 20 tags an object 70 with the radiant pointing device 30 and thence enters particular metadata pertinent to that object 70 and associable with the particular unique object location 76. The metadata pertinent to the object 70 is uploaded as object data 78 by the originating user 20, which object data 78 will be accessible to other users when they subsequently tag the object 70 with their radiant pointing devices 30. Metadata includes all data uploadable by a user, including executable files (where extant) deliverable over network to matched unique locations of users operating in the network relative object locations stored in memory and accessible over the network. Originating users may restrict read-only access to object data for objects originated to the system. Object data may include daily specials, discounts, special offers, information, instructions, video and/or audio clips, or other data pertinent to an object and storable and accessible over network.

A user may effect a tag to an object by entering a proximal range of an object without use of the radiant pointing device, whereby determinable proximity to objects enables access to object data. Thus, for example, proximity to a menu may enable access to the special of the day, for example, or a particular coupon, say, pushed to the WCD determined to be within the proximal range of a relevant object.

Figure 6:
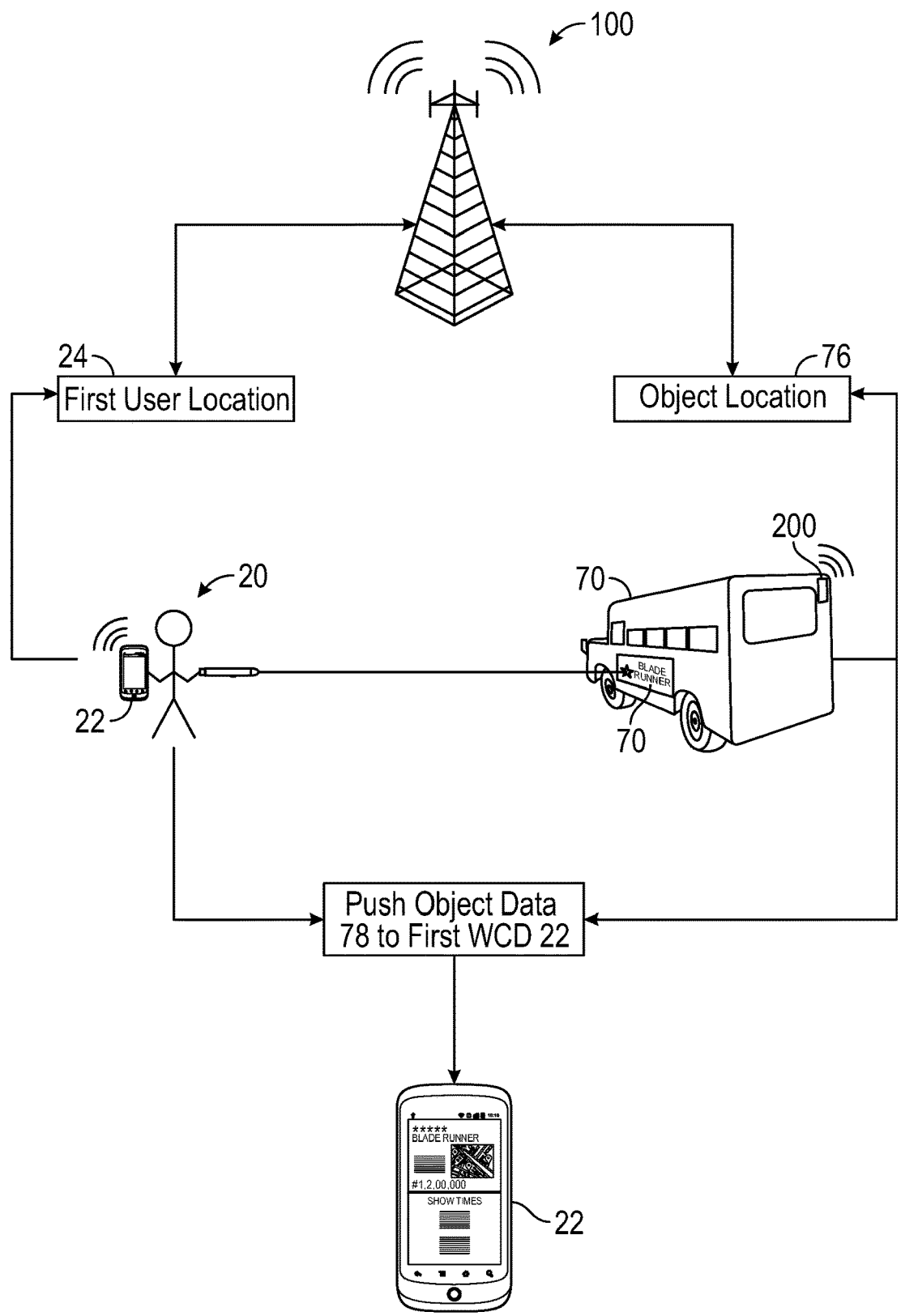
FIG. 6 is a diagrammatic view of a user tagging an object having a unique object location determinable over network by action of an object WCD whereby the user is enabled download of object data to the user WCD.
Figure 7:
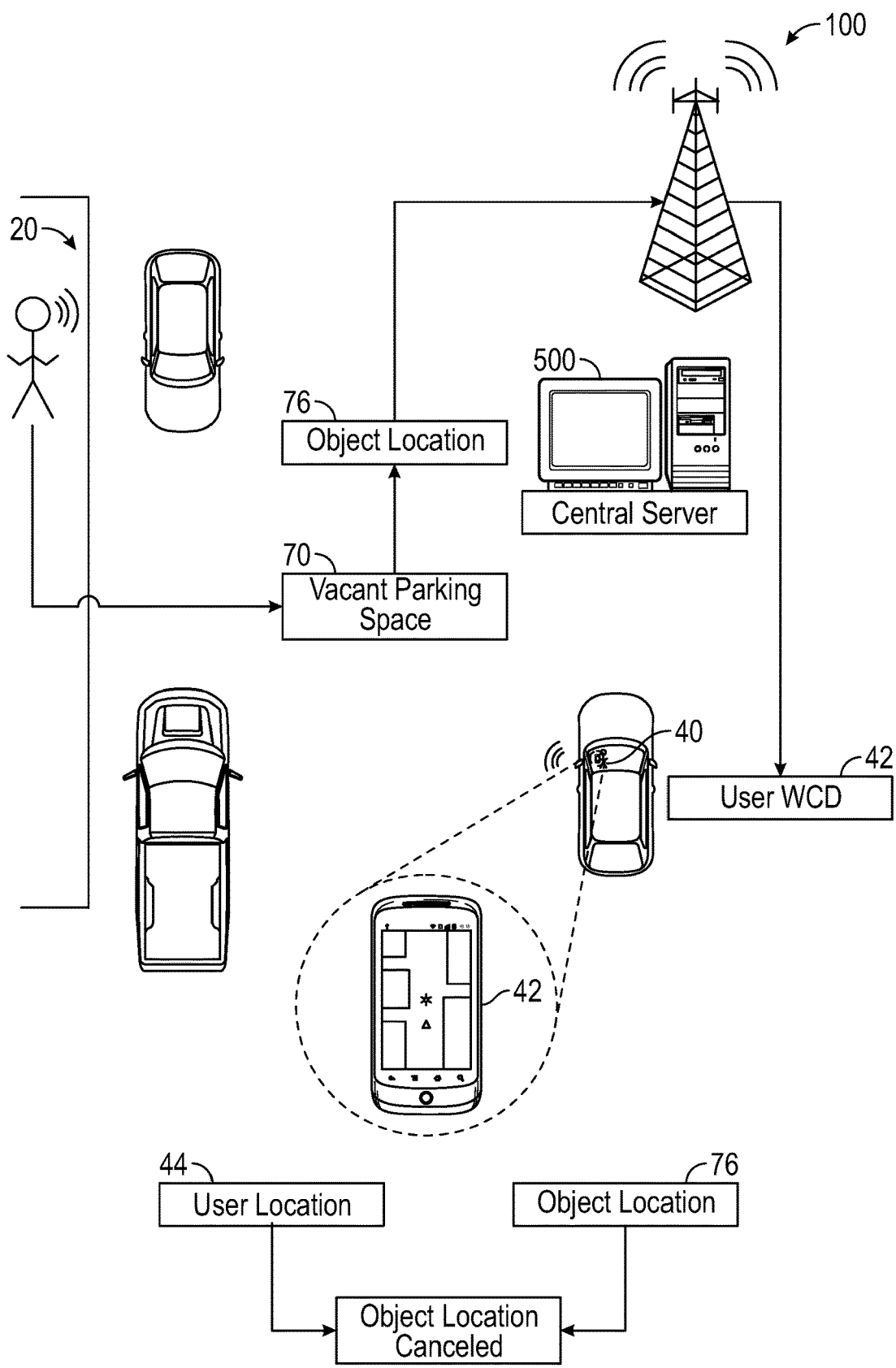
FIG. 7 is a diagrammatic view of an example embodiment of a parking mode whereby vacant parking space availability is sharable over network and updatable by users alternately occupying and vacating said parking spaces.
Figure 8:
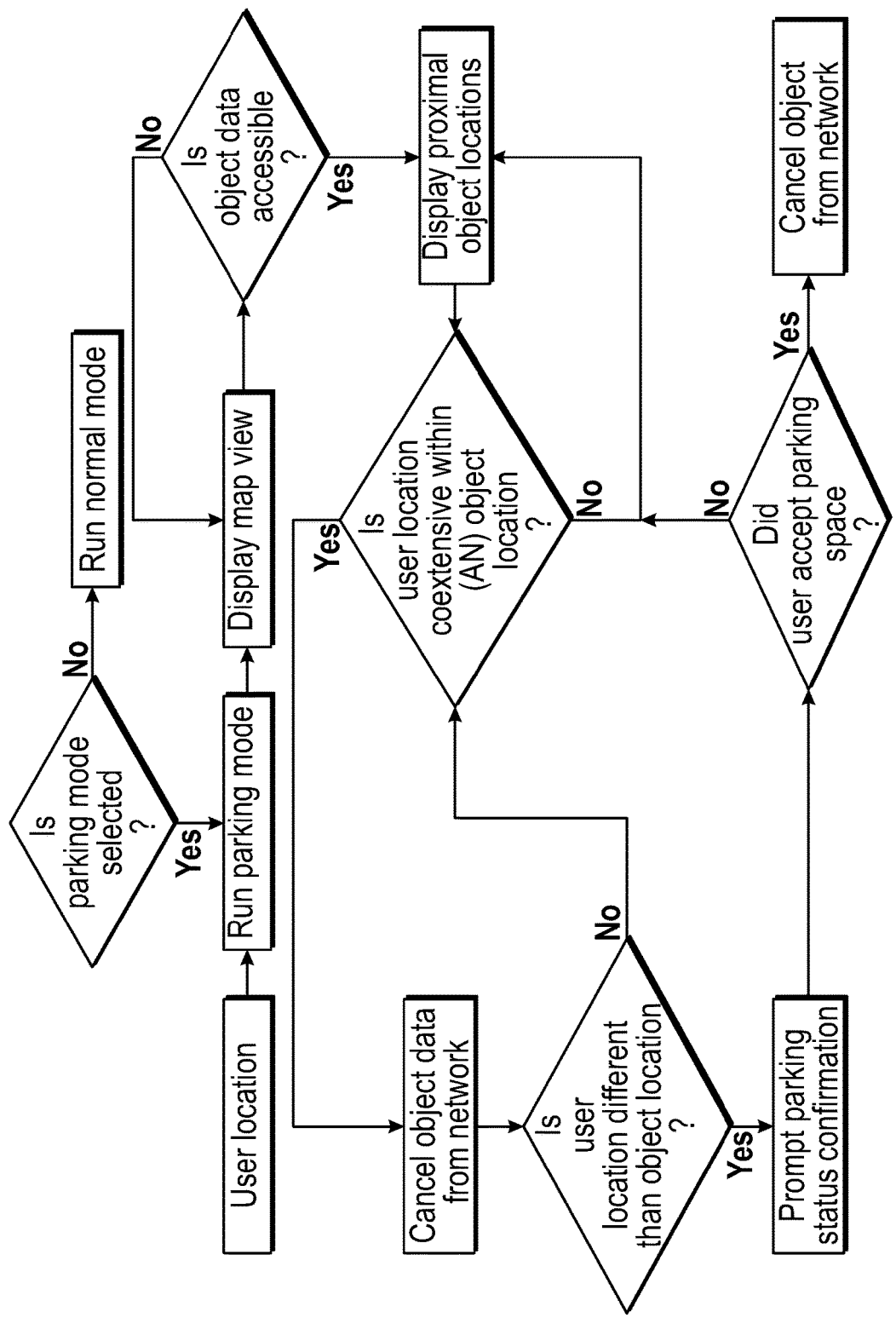
FIG. 8 is a flow diagram view of an example embodiment of a parking mode operable on WCDs participating in the system.

As shown in FIG. 6, an object WCD 200 may transmit the unique object location 76 and control object data associated with the object 70 whereby use of the object WCD 200 controls object data 78 associated with a particular object 70 for access to users tagging the object 70. In the example shown in FIG. 6, the object 70 is an advertisement on the side of a moving bus. The object WCD 200 in this example is incorporated with the bus navigation system. The bus's location is thus discoverable over the network 100 in real-time, whereby tagging of the advertisement on the side of the bus by the first user 20 enables determination of the first user location 24 relative the object location 76. Effecting a tag to the advertisement upon the bus (the object 70) thus enables access to object data 78 downloadable to the first WCD 22 whereby information is relayable to the specific user (the first user 20) tagging the object 70, in this instance an advertisement for a movie. In this instance the object data 78 accessible to the first user 20 subsequent tagging of the advertisement includes receipt of an updated RSS feed for a particular movie review deliverable in real-time, current box office take displaying as real-time data, and, also, locations proximal the user where the movie is playing with associated showtimes.

The first user may likewise use the radiant pointing device to tag at least a second user. When the unique second user location, determined over network, is determined to match the vector presented by the radiant pointing device in use of the first user, at least a portion of the second user profile data may be displayable on screen of the first WCD. The portion of the second user profile data may include a status notification. The status notification may be a denial to share information. The second user may receive a tag prompt signaling to the second user they have been tagged. At least a portion of a first user profile data may display upon the second WCD as part of the tag prompt. Additionally, the first user may push a tag prompt to the second user when tagging the second user, whereby a particular signal, message, or alert may be issued from the second WCD when the second WCD is set to accept such tag prompts from tagging users. Thus line of sight communication between users participating in the network is enabled. Tag prompts may establish P2P between WCDs when accepted by each user to establish P2P communication.

Figure 9:
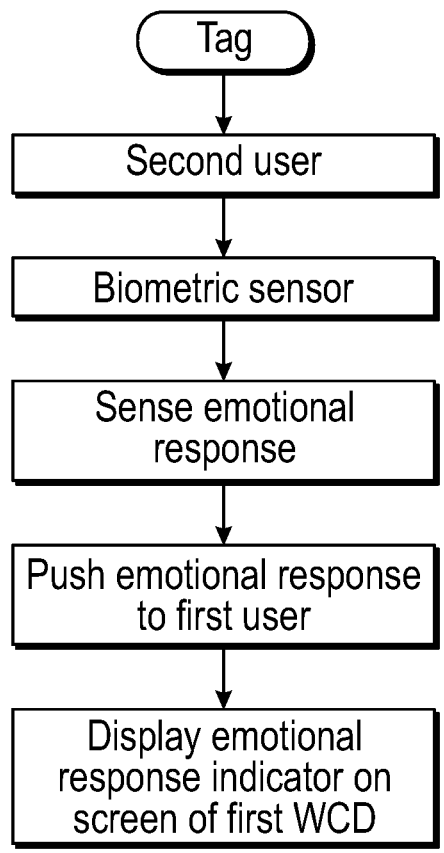
FIG. 9 is a flow diagram of an example embodiment of a shared emotional response sensed by at least one biometric sensor disposed in operational contact with a second and pushed back to a first user.

In at least one embodiment contemplated for use with the present system, at least one biometric sensor may be disposed in sensing communication with each user (see for example FIG. 9). The at least one biometric sensor may be devised to register an emotional response from the user whereby said emotional response may be communicated over network between participating users. Thus a first user tagging a second user, for example, may receive a response push notification from the second user indicative of an emotional response to a tag or other communication effected between said first and second user. The emotional response may be signaled by an increase in user pulse, for example, and may be displayable as heartbeats per minutes, for example, on the user WCD.

Users are further enabled to share information dependent on unique location data. For example, as depicted in the example embodiment illustrated in FIGS. 7 and 8, a parking mode is contemplated as an embodiment of the present system 10. In this example, an originating user 20 may tag a vacant parking space 70 and upload the vacant parking space location 76 over network 100 whereby other users 40 may view the location of the vacant parking space. In this instance, the object location 76 corresponds to the position of a vacant space (the object 70) and users operating WCDs over the network 100 are thereby apprised of the location of the vacant parking space. In this instance, the uploaded object data 78 (in this instance, the vacancy of the parking space and a corresponding location) is read-write accessible to users whereby a user determined to be occupying the parking space may disable the object data 78 from network accessibility whereby the parking space vacancy is no longer shown over the network to other users. In this example embodiment, automatic cancellation of the object data 78 from the network 100 may be effected when a unique user location 44 is matched to the unique object location 76 (i.e. when a particular user is occupying the same location as the tagged vacant parking space).

An onscreen parking status confirmation prompt on the user WCD 42 may signal to the user to accept cancellation of the object data from the network and thus remove the parking space vacancy from display over network. Before vacating the space (i.e. upon a user's return to the object location whereby said user location is coextensive with the object location a second time) a user may be prompted with a parking status confirmation to confirm they are vacating the parking space whereby the object data 78 is again automatically rendered accessible over network. In such an embodiment, a parking mode of operation of the present system 10 may be selectable upon the user WCD to display a map view detailing available vacant parking spaces in the vicinity of the user, whereby user location effects update to object locations displayable as vacant parking spaces upon the map view accessible over network.

What is claimed is:

1. A proximity enabled communication network system for peripheral device comprising:
    at least a first wireless communications device (WCD) in operation by a first user, said at least first WCD configured in networked communication with a central server, said at least first WCD discoverable over network by transmission of repeating signals whereby a unique first user location is continuously determinable; and
    at least one radiant pointing device configured in wireless communication with the at least first WCD, said at least one radiant pointing device having a directionally sensitive member disposed sensible of a vector when a directable radiant emission, wieldable by the first user to tag objects, is sensed incident an object;
    wherein a unique object location of any object determined incident the directable radiant emission is sensible to the at least first WCD and object data pertinent to said object is uploadable to the central server and downloadable therefrom for display on the at least first WCD when said object is subsequently tagged.

2. The proximity enabled communication network system for peripheral device of claim 1 further comprising at least a second WCD configured in networked communication with the central server, said second WCD having a unique second user location determinable over network and thereby discoverable to be within a proximal range of the at least first WCD, whereby discovery of said at least second WCD within the proximal range of the at least first WCD prompts selectable near field communication (NFC) and peer-to-peer (P2P) communication between at least the first user and a second user.

3. The proximity enabled communication network for peripheral device of claim 2 wherein the presence of the at least second WCD is displayable onscreen as occurring within the determinable proximal range of the at least first WCD when said at least second WCD is sensed operating within the proximal range, whereby at least a portion of a profile data of the second user accessible over network is displayable on the at least first WCD to the first user.

4. The proximity enabled communication network for peripheral device of claim 3 wherein the first user may tag the second user with the radiant pointing device to match the unique second user location determined over network to a location relative to the first WCD whereby at least a portion of the profile data of the second user is displayable onscreen of the first WCD and establishment of NFC and P2P communication may thereafter be prompted.

5. The proximity enabled communication network for peripheral device of claim 4 wherein at least a portion of the profile data of the second user is displayable on the at least first WCD when the first user tags the second user.

6. The proximity enabled communication network for peripheral device of claim 5 wherein at least a portion of the profile data of the first user is displayable onscreen of the second WCD device when the first user tags the second user.

7. The proximity enabled communication network for peripheral device of claim 6 wherein the first WCD pushes a status message to the second WCD when the first user tags the second user.

8. The proximity enabled communication network for peripheral device of claim 7 wherein at least one biometric sensor, disposed in sensing communication with the second user, reads an emotional response communicable to the second WCD and thence communicable to the first WCD to convey the emotional response to the first user.

9. A proximity enabled communication network system for peripheral device operable in line-of-sight and determined by locational proximity, said system comprising:
    at least a first wireless communications device (WCD) in operation by a first user, said at least first WCD configured in networked communication with a central server, said at least first WCD discoverable over network by transmission of repeating signals whereby a unique first user location is continuously determinable;
    at least a second WCD configured in networked communication with the central server, said second WCD discoverable over network by transmission of repeating signals whereby a unique second user location is continuously determinable and discoverable to be within a determinable proximal range of the at least first WCD, whereby discovery of said at least second WCD within the proximal range prompts selectable near field communication (NFC) and peer-to-peer (P2P) communication between at least the first user and a second user;

at least one radiant pointing device disposed in wireless communication with the at least first WCD, said at least one radiant pointing device having directable radiation wieldable by the first user to tag objects sensed incident said directable radiation whereby a unique object location is determinable relative to the first user;

wherein the unique location of any object determined incident the directable radiation is sensible to the at least one WCD and metadata pertinent to said object and previously uploaded to the central server is thence displayable on the at least one WCD as object data to the user wielding the radiant pointing device; and wherein the first user may tag the second user with the radiant pointing device to match the unique second user location determined over network to a location relative the first WCD whereby at least a portion of the profile data of the second user is displayable onscreen of the first WCD and establishment of NFC and P2P communication between the first and second users may be prompted.

10. The proximity enabled communication network for peripheral device of claim 9 wherein the at least second WCD is displayable onscreen as occurring within the determinable proximal range of the at least first WCD when said at least second WCD is sensed operating within the proximal range, whereby at least a portion of a profile data of the second user accessible over network is displayable on the at least first WCD to the first user.

11. The proximity enabled communication network for peripheral device of claim 10 wherein at least a portion of the profile data of the second user is displayable on the at least first WCD when the first user tags the second user.

12. The proximity enabled communication network for peripheral device of claim 11 wherein at least a portion of the profile data of the first user is displayable onscreen of the second WCD device when the first user tags the second user.

13. The proximity enabled communication network for peripheral device of claim 12 wherein the first WCD pushes a status message to the second WCD when the first user tags the second user.

14. The proximity enabled communication network for peripheral device of claim 13 wherein at least one biometric sensor, disposed in sensing communication with the second user, reads an emotional response of the second user communicable to the second WCD and thereby communicable to the first WCD to convey the emotional response to the first user.

* * * * *